(12) United States Patent
Allert et al.

(10) Patent No.: US 11,015,166 B2
(45) Date of Patent: May 25, 2021

(54) FRUSTULES EXTRACTED FROM BENTHIC PENNATE DIATOMS HARVESTED FROM AN INDUSTRIAL BIOFILM PROCESS

(71) Applicant: SWEDISH ALGAE FACTORY AB, Gothenburg (SE)

(72) Inventors: Sofie Allert, Gothenburg (SE); Angela Wulff, Vänersnas (SE)

(73) Assignee: SWEDISH ALGAE FACTORY AB, Gothenburg (SE)

( * ) Notice: Subject to any disclaimer, the term of this patent is extended or adjusted under 35 U.S.C. 154(b) by 131 days.

(21) Appl. No.: 16/209,993

(22) Filed: Dec. 5, 2018

(65) Prior Publication Data
US 2019/0106672 A1    Apr. 11, 2019

Related U.S. Application Data

(63) Continuation of application No. PCT/EP2017/063851, filed on Jun. 7, 2017.

(30) Foreign Application Priority Data

Jun. 8, 2016  (SE) .................................... 1650803-8

(51) Int. Cl.
| | | |
|---|---|---|
| C12N 1/12 | (2006.01) | |
| C12P 3/00 | (2006.01) | |
| H01L 51/42 | (2006.01) | |
| H01L 31/0216 | (2014.01) | |
| H01L 51/00 | (2006.01) | |
| H01G 9/20 | (2006.01) | |

(52) U.S. Cl.
CPC .................. *C12N 1/12* (2013.01); *C12P 3/00* (2013.01); *H01L 31/02167* (2013.01); *H01L 31/02168* (2013.01); *H01L 51/0093* (2013.01); *H01L 51/4213* (2013.01); *C12N 2500/05* (2013.01); *H01G 9/209* (2013.01)

(58) Field of Classification Search
CPC ........ C12N 1/12; C12N 2500/05; C12N 1/36; C12N 2510/00; C12N 5/0654; C12P 3/00; H01G 9/209; H01L 31/02167; H01L 31/02168; H01L 51/0093; H01L 51/4213; A61K 47/6901; A61K 9/0024; A61K 2035/126; A61K 47/46; A61L 2300/258; A61L 27/54; A61L 31/16; A61L 27/3608; A61L 27/3808; B33Y 80/00; A61P 43/00; A61P 19/00; A61P 3/00; G01N 33/48; G06F 19/3468; Y02A 50/411; Y02A 90/26; Y02E 10/549; Y02P 60/12; C12R 1/89
See application file for complete search history.

(56) References Cited

U.S. PATENT DOCUMENTS

| | | | |
|---|---|---|---|
| 8,877,465 B2 * | 11/2014 | Geiringer | ................ A61P 17/02 |
| | | | 435/134 |
| 2006/0246277 A1 | 11/2006 | Axtell, III | |
| 2015/0338403 A1 | 11/2015 | Wang | |

FOREIGN PATENT DOCUMENTS

| | | |
|---|---|---|
| CN | 104480014 | 4/2015 |
| KR | 20150027504 | 3/2015 |
| TW | 201539839 A | 10/2015 |

OTHER PUBLICATIONS

Umemura K. et al: "Diatom Cells Grown and Baked on a Functionalized Mica Surface", Journal of BIOIOGI Cal Physics, vol. 34, No. 1-2, Jun. 24, 2008 (Jun. 24, 2008), pp. 189-196, XP019644802, ISSN: 1573-0689, DOI: 10.1007/S10867-008-9086-Z.

Debenest T. et al: "Herbicide effects on freshwater benthic diatoms: Induction of nucleus alterations and silica cell wall abnormalities". Aquatic Toxicology. vol. 88. No. 1, Jun. 2, 2008 (Jun. 2, 2008), pp. 88-94, XP022650566, ISSN: 0166-445X, DOI: 10.1016/J.AQUATOX.2008.03.011.

Debenest T. et al: "A new cell primo-culture method for freshwater benthic diatom communities". Journal of Applied Phycology. vol. 21, No. 1, May 14, 2008 (May 14, 2008). pp. 65-73. XP019678353, ISSN: 1573-5176.

Chauton M. K. et al: "Titanium uptake and incorporation into silica nanostructures by the diatom *Pinnularia* sp. (Bacillariophyceae)". Journal of Applied Phycology, vol. 27, No. 2, Jul. 24, 2014 (Jul. 24, 2014), pp. 777-786, XP035477841, ISSN: 0921-8971, DOI: 10.1007/S10811-014-0373-8.

Chen X. et al: "Numerical and experimental investigation of light trapping effect of nanostructured diatom frustules". Scientific Reports, vol. 5. No. 1. Jul. 9, 2015 (Jul. 9, 2015), XP055397141. DOI: 10.1038/srep11977.

Viji S. et al: "Diatom-Based Label-Free Optical Biosensor for Biomolecules". Applied Biochemistry and Biotechnology, vol. 174. No. 3. Jul. 3, 2014 (Jul. 3, 2014), pp. 1166-1173. XP035399361. ISSN: 0273-2289. DOI: 10.1007/S12010-014-1040-X.

Yang J. et al: "Ultra-sensitive immunoassay biosensors using hybrid plasmonic-biosilica nanostructured materials". Journal of Biophotonics, vol. 8, No. 8, Sep. 25, 2014 (Sep. 25, 2014), pp. 659-667, XP055397136, DE ISSN: 1864-063X. DOI: 10.1002/jbio.201400070.

Lebeau T. et al: "Diatom cultivation and biotechnologically relevant products. Part I: cultivation at various scales". Applied Microbiology and Biotechnology. vol. 60, No. 6, Dec. 13, 2002 (Dec. 13, 2002), pp. 612-623, XP055018110, ISSN: 0175-7598. DOI: 10.1007/s00253-002-1176-4.

(Continued)

*Primary Examiner* — Deborah K Ware
(74) *Attorney, Agent, or Firm* — Duane Morris LLP; Gregory M. Lefkowitz; Jiazhong Luo

(57) ABSTRACT

A method of extracting frustules from benthic pennate diatoms is disclosed. The method includes culturing benthic pennate diatoms in an industrial biofilm process, wherein in the industrial biofilm process the benthic pennate diatoms are growing on at least one surface in a water-containing compartment and wherein the benthic pennate diatoms forms a biofilm on the at least one surface; harvesting the benthic pennate diatoms from the at least one surface; and extracting the frustules by separating the frustules from organic biomass contained in the benthic pennate diatoms.

9 Claims, 4 Drawing Sheets

(56) References Cited

OTHER PUBLICATIONS

Lebeau et al: "Diatom cultivation and biotechnologically relevant products. Part II: current and putative products". Applied Microbiology and Biotechnology. vol. 60, No. 6, Dec. 13, 2002 (Dec. 13, 2002), pp. 624-632, XP055018109, ISSN: 0175-7598. DOI: 10.1007/s00253-002-1177-3.

* cited by examiner

FRUSTULES EXTRACTED FROM BENTHIC PENNATE DIATOMS HARVESTED FROM AN INDUSTRIAL BIOFILM PROCESS

This application is a continuation of International Application No. PCT/EP2017/063851, filed 7 Jun. 2017, which claims the benefit of Swedish Patent Application No. SE 1650803-8, filed 8 Jun. 2016, the entire contents of which are hereby incorporated by reference.

TECHNICAL FIELD OF THE INVENTION

The present invention relates to frustules extracted from benthic pennate diatoms which benthic pennate diatoms have been harvested from an industrial biofilm process and the use of such frustules extracted from benthic pennate diatoms.

BACKGROUND OF THE INVENTION

Diatoms, a type of algae which are present in both fresh water and marine environments, comprise a frustule which have a high content of silicon dioxide. The frustules are a source for a nanoporous silicon dioxide material which can be used in various applications. Diatoms are not only a reserve for silicon, in their fossil form they serve as a reserve for oil, coal and phosphorous. Moreover, diatoms produces a large amount of the oxygen we breath every day.

There are a variety of different types of diatoms and they are usually classified according to their size and/or shape as well as their living environment in the water.

There are many examples where diatoms frustules has been used in various applications. For example Chen et al. (Scientific Reports 2015, DOI: 10.1038/srep11977) shows how the light trapping effect of diatom frustules can be used for enhancing the power conversion efficiency in solar cells. Further, US 2015/0338403 A1 shows a composition of diatom frustules and a metal coating. US 2015/0367322 A1 describes a method for forming a diatom-based nano composite. Moreover, Lim et al. (J. Appl. Phys. 2015, 27, 763, DOI: 10.1007/s10811-014-0356-9) describe how frustule from diatoms can be used for protein absorption.

There is a need for improving the state of the art to provide diatom frustules in large quantities of a high quality allowing for use of frustules extracted from diatom in many different applications, e.g. solar cells, biosensors, composite materials and/or sound isolation.

SUMMARY OF THE INVENTION

It is an object of the present invention to improve the current state of the art, and to at least alleviate the above mentioned problems. This and other objects are achieved by frustules extracted from benthic pennate diatoms which have been harvested from an industrial biofilm process and the use of such frustules extracted from benthic pennate diatoms.

The inventors realized that frustules extracted from benthic pennate diatoms cultured through an industrial biofilm process may be used for various applications such as e.g. uptake of energy, chemicals and/or mechanical waves by for example light trapping properties. For example, the frustules may be used for enhancing the efficiency of solar cells due to the light trapping properties of the frustules. In the industrial biofilm process the benthic pennate diatoms are grown on a surface in a water compartment and wherein said benthic pennate diatoms are harvested from said surface.

According to a first aspect of the present invention a method for extracting frustules from benthic pennate diatoms is provided. The method comprises the steps of:

culturing benthic pennate diatoms in an industrial biofilm process, wherein in said industrial biofilm process said benthic pennate diatoms are growing on at least one surface in a water-comprising compartment and wherein said benthic pennate diatoms forms a biofilm on said at least one surface;

harvesting said benthic pennate diatoms from said at least one surface;

extracting said frustules by separating said frustules from organic biomass comprised in said benthic pennate diatoms.

The present invention is based on the realization that the industrial biofilm process provides a controlled way to grow and harvest the desired species of benthic pennate diatom which will provide frustules with specific properties. Culturing the benthic pennate diatoms in an industrial biofilm process facilitates the harvesting of such benthic pennate diatoms as compared with harvesting the benthic pennate diatoms from marine environments and/or from fresh water lakes. Moreover, the purity of the benthic pennate diatoms cultured in an industrial biofilm process is higher than the purity of the benthic pennate diatoms from marine environments and/or from fresh water lakes. The industrial biofilm process for culturing benthic pennate diatoms will ensure a high and even quality of the frustules extracted from benthic pennate diatoms.

The speed of which the diatoms, e.g. benthic pennate diatoms, grows can be divided into three phases, A first phase where the diatoms grows slowly, a second phase where the diatoms grow exponentially and a third phase where the grow has stagnated or almost stopped. In which phase of the diatoms are depends on the size or concentration of diatoms in a certain population. The size of the industrial biofilm process allows for providing the diatoms in the second phase and therefore the fastest growth of the benthic pennate diatoms may be achieved. According to one theory, culturing of diatoms in a smaller water compartment may provide the diatoms only, or mainly, in the first phase and therefore the growth of the diatoms may be slower.

Benthic pennate diatoms may have thicker frustules than other diatoms which makes them more durable than frustules from other diatoms. In other words, the benthic pennate diatoms are more heavily silicified than other diatoms. Compared to centric diatoms, pennate diatoms are also easier to cultivate industrially in larger scale mainly because of the fact that they have no need of sexual reproduction. Compared to the centric diatoms the pennate diatoms grow faster which make them more appropriate for an up scaled production. The frustule of the benthic pennate diatom constitutes approximately between 15% and 30% of the diatom, far more than pelagic (suspension living) pennate diatoms and centric diatoms which makes the frustules from benthic pennate diatoms more durable under the extraction process. In other words, the frustules of the benthic pennate diatoms are less likely to crack or break during the extraction process than frustules from other types of diatoms due to the thickness of the frustules. Hence, structures of the frustules may be kept under handling or use of them.

It shall be understood that the benthic means that the diatoms claimed is living on and/or in aquatic soft and hard bottom substrates, including ice. For example, benthic pennate diatoms may grow on stones, in the bottom sediment or on other surfaces which are covered with water. Benthic pennate diatoms are not suspension living diatoms. Further, it should be understood that pennate means that the diatoms claimed is bilateral symmetric.

According to at least one example embodiment the industrial biofilm process is a horizontal biofilm process, i.e. the surfaces on which the benthic pennate diatoms grows on are horizontal surfaces.

It should be understood that the term "horizontal surface" is referring to a surface comprising a plane which is substantially parallel to the horizon, i.e. the surface has a main extension in a horizontal manner. The horizontal surface may be substantially orthogonal to a vertical surface.

According to at least one example embodiment the benthic pennate diatoms forms during cultivation a biofilm on the surface in the water-compartment. The biofilm may for example be a still biofilm. Additionally, or alternatively, the biofilm formed by the benthic pennate diatoms may be cultivated on top of circulating horizontal surfaces.

According to at least one embodiment of the invention, the benthic pennate diatoms are cultured on a quadratic or rectangular surface. The surface may for example be 1*1 m (i.e. 1 m*1 m, or 1 m²), or at least 1 m².

According to at least one example embodiment, the width of the surface on which the benthic pennate diatoms are being cultured may be at least 0.5 m. or 0.75 m, or 1 m, or 1.5 m. According to at least one example embodiment of the invention, the width of the surface on which the benthic pennate diatoms are being cultured may be no longer than 3 m, or 2 m, or 1.5. Stated differently, the width of the surface on which the benthic pennate diatoms are being cultured are within an interval of 0.5-3 m, or 0.75-2 m, or 1-2 m.

According to at least one example embodiment, the length of the surface on which the benthic pennate diatoms are being cultured are at least 0.5 m, or 1 m, or 2 m, or 3 m, or 5 m. According to at least one example embodiment, the length of the surface on which the benthic pennate diatoms are being cultured is no longer than 10 m, or 8 m, or 7 m, or 6 m, or 5. Stated differently, the length of the surface upon which the benthic pennate diatoms are being cultured may be within the interval of 0.5-10 m, or 1-7 m, or 1-6 m. Hereby, a desirable size of the surface is provided.

According to at least one example embodiment of the invention several surface on which the benthic pennate diatoms are being cultured on may be stacked upon each other such that the benthic pennate diatoms is cultured on different levels within the water compartment. In such way, the surface area available for culturing benthic pennate diatoms is increased with in the same water compartment.

According to at least one example embodiment of the invention, the industrial biofilm process comprises several water-comprising compartments which may be stacked on top of each other or placed side-by-side.

According to at least one example embodiment of the invention, several surfaces may be connected to each other such that a larger surface is achieved.

According to at least one example embodiment of the invention, the surface upon which the benthic pennate diatoms are being cultured on may be of any other geometric form than quadratic or rectangular. It may for example be triangular or circular. Additionally, or alternatively the surface upon which the benthic pennate diatoms are being cultured upon may be in the form of a star.

According to at least one example embodiment, the water-comprising compartment is a pool. In other words, the method comprises the step of culturing benthic pennate diatoms in a pool or a basin. According to at least one example embodiment, said pool is a shallow pool wherein the depth of water is at least 0.2 m, or at least 0.3 m, or at least 0.5 m. or at least 1 m. Additionally, or alternatively, the depth of water in said pool is no more than 2 m, or no more than 1 m, or no more than 0.5 m. For example, the depth of water may be 0.2-2 m, or 0.3-1 m.

According to at least one example embodiment of the invention, the water-compartments in which the surfaces for cultivation of benthic pennate diatoms is arranged may comprise at least 2 L of water, or 5 L of water, or 10 L of water, or at least 20 L of water, or at least 30 L of water.

According to at least one example embodiment of the invention the frustules are extracted from the organic biomass of the benthic pennate diatoms after the benthic pennate diatoms have been harvested from the industrial biofilm process. In other words, the benthic pennate diatoms are harvested from the surface on which they have been cultured on and then subsequently the organic biomass is removed from the frustules. Stated differently, the frustules and the organic biomass of the benthic pennate diatoms are separated after the benthic pennate diatoms have been harvested from the surface upon which they have been cultured on.

According to at least one example embodiment of the invention the frustules can be extracted via a calcination process. In such a process the benthic pennate diatoms are being heated until the organic biomass of the diatoms is burnt away leaving the frustules. Additionally, or alternatively, the organic biomass may be removed by the use of hydrogen peroxide.

According to at least one example embodiment of the invention the temperature of the calcination process is no higher than 450° C. Keeping the temperature below this temperature may hinder etching of the frustules. In other words, keeping the temperature below 450° C. allows for keeping the thickness and/or the structure of the frustules.

According to at least one example embodiment of the invention the industrial biofilm process comprises the benthic pennate diatoms being provided to a water compartment. The water compartment may subsequently be provided with nutritious water. In other words, the method may comprise the step of culturing benthic pennate diatoms in a water-comprising compartment comprising nutritious water. The nutritious water makes it possible for the benthic pennate diatoms to grow on a surface provided in the water compartments. According to at least one example embodiment, the benthic pennate diatoms are being harvested after a predetermined time. How long said time is depends on several parameters such as light intensity. The term nutritious water shall here be understood as water comprising mainly nitrogen (N), e.g. added in the form of $NO_3$ and phosphorus (P), e.g. added in the form of $PO_4$.

The concentration of nitrogen (N) in the nutritious water is 0.01-500 g/m³, or preferably 25-250 g/m³. The concentration of phosphorus (P) is 0.01-100 g/m³ or 2-20 g/m³. The nitrogen and/or phosphorus is dissolved in the water in bioavailable forms. The amount of nitrogen and phosphorus may affect the productivity of the diatoms and thereby the efficiency of the industrial biofilm process.

According to at least one example embodiment of the invention the nutritious water may be received from a fish farm. Additionally, or alternatively, the nutritious water may be achieved from waste water from e.g. food industry, biomass related industries, or households. Additionally, or alternatively, the nutritious water may be achieved by adding nitrogen and phosphorus and other nutrients necessary for algal growth to sea water or fresh water.

According to at least one example embodiment of the invention, the method further comprises the step of adding a silicon compound, e.g. $Na_2SiO_3 \cdot 5H_2O$ or $Na_2SiO_3 \cdot 9H_2O$ to the water in said water-comprising compartment such that the concentration of silicon (Si) in the water in said water-comprising compartment is in the range of 0.01-100 g/m$^3$. More preferably, the concentration of silicon (Si) in the water in the water-comprising compartment is 1.5-15 g/m$^3$. When these compounds are dissolved in the water, silicis acid $Si(OH)_4$ is formed. The amount of added silicon affects the thickness of the frustules. Too much of the silicon compounds may give silicon oxide precipitation. The silicon oxide precipitation may lower the purity of the extracted frustules.

According to at least one embodiment of the invention, the ratio between nitrogen, phosphorus and silicon is 16:1:15.

According to at least one example embodiment of the invention the frustules extracted from benthic pennate diatoms used are extracted from fresh benthic pennate diatoms. This means that the frustules are not fossil frustules. The frustules which have been extracted from fresh benthic pennate diatoms have a higher porosity than fossil frustules. Moreover, the frustules extracted from fresh benthic pennate diatoms are of a higher purity than fossil frustules.

According to at least one example embodiment of the invention, use of frustules extracted from benthic pennate diatoms wherein said frustules extracted from benthic pennate diatoms are provided in a liquid medium and/or as a dry product. In other words, said method comprises the step of providing said frustules in a liquid medium and/or as dry product. According to at least one example embodiment of the invention the frustules extracted from benthic pennate diatoms are provided in a liquid medium. The frustules extracted from benthic pennate diatoms can e.g. be provided as a solution, as a suspension, as a dispersion and/or as a gel.

According to at least one example embodiment of the invention the liquid medium may be solvents of various types, e.g. water.

According to at least one example embodiment of the invention the one or more additional substances can be added to the liquid medium in which the benthic pennate diatoms are being provided. Such substances may be for example polymers.

According to at least one example embodiment of the invention the frustules extracted from benthic pennate diatoms are provided as a dry product. Examples of such dry products are powders and/or aerogels. Aerogels is a gel where the fluid medium is changed from a liquid to a gas.

According to at least one example embodiment of the invention the frustules extracted from benthic pennate diatoms as being provided as a dry product can be used in composites where the frustules extracted from benthic pennate diatoms are mixed with another material. Examples of such material can for example be polymers and/or metals. According to at least one example embodiment of the invention, said composite may be provided on top of a solar cell or a solar panel. It may be understood that the term "composite" here refers to a composite material, i.e. a material made from two or more constituent materials with different physical or chemical properties that, when combined, produce a material with characteristics different from the individual components.

According to at least one example embodiment of the invention the frustules extracted from benthic pennate diatoms provided in a liquid medium is deposited on a surface using a coating method. According to at least one example embodiment, the liquid medium is a polymer solution comprising said frustules.

According to at least one example embodiment of the invention the coating method used is chosen from a list comprising but not limited to: doctor blading, spin-coating, roller coating, screen printing, spray coating and dip coating.

According to at least one example embodiment of the invention the frustules extracted from benthic pennate diatoms provided in a liquid medium can be provided as a monolayer or as several layers on top of each other with the above mention and other coating methods. The number of layers may depend on the application.

According to at least one example embodiment of the invention the frustules extracted from benthic pennate diatoms provided in a liquid medium can be provided in a layer with a thickness in the range of 1 µm to 1000 µm, or more preferably between 1 µm to 100 µm.

According to at least one example embodiment of the invention frustules extracted from benthic pennate diatoms are used for uptake of energy, chemical substances and/or mechanical waves. In other words, the method further comprises the step of using the frustules extracted from benthic pennate diatoms are used for uptake of energy, chemical substances and/or mechanical waves.

It shall be understood that with "uptake of energy, chemical substances and/or mechanical waves" it means that the frustules traps or capture or absorb the energy, chemical substance and/or the mechanical waves. For example, uptake of energy may be trapping of light, that is e.g. enhancing the light absorbance comparing not using such frustules. Moreover, it shall be understood that the energy, chemical substance and/or mechanical waves may be transported, or guided through the frustules.

According to at least one example embodiment of the invention the uptake of energy, chemical substances and/or mechanical waves makes the frustules extracted from benthic pennate diatoms useful in many applications.

According to at least one example embodiment of the invention the uptake of energy can be released from the frustules extracted from benthic pennate diatoms. According to at least one example embodiment of the invention the frustules extracted from benthic pennate diatoms can be used in energy storage applications due to the capability to uptake and release of energy.

According to at least one example embodiment of the invention the energy is radiation. The radiation may be heat and/or light. The light may comprise wavelengths within the infrared range, the visible range and/or the ultraviolet range. According to at least one example embodiment of the invention the chemical substances are e.g. water and/or proteins.

According to at least one example embodiment of the invention the mechanical waves are sound waves.

According to at least one example embodiment of the invention the frustules extracted from benthic pennate diatoms traps energy which corresponds to wavelengths within the infrared range, within the visible range and/or within the ultraviolet range, and wherein said uptake of energy is used for enhancing the efficiency in solar cells. In other words, the method comprises the step of using said frustules extracted from benthic pennate diatoms for uptake of energy within the infrared range, within the visible range and/or within the ultraviolet range, and wherein said uptake of energy is used for enhancing the efficiency in solar cells.

According to at least one example embodiment of the invention the frustules may manipulate the light which has been up taken such that spectral properties of the light changes. In other words, the frustules may change the wavelength of the light which has been captured or trapped.

According to at least one example embodiment of the invention, the funnel-like structure of said frustules may manipulate the spectral properties of the light.

According to at least one example embodiment of the invention, the frustules extracted from benthic pennate diatoms is built up by several layers of nanoporous silicon dioxide, i.e. silica. For example, the number of layers may be 2, or 3, or 4. Nanoporous means that the silicon dioxide layers comprise pores with a diameter in the range of 10-500 nm, or in the range of 20-300 nm, or in the range of 30-200 nm.

According to at least one example embodiment of the invention, the pores of the different layers of the frustules may have different sizes. Typically, the top layer comprises the largest pores whereas the lowest layer comprises the smallest pores. The sizes of the pores of the different layers may typically decrease for each layer starting from the top layer and moving through the layers to the lowest layer.

According to at least one example embodiment of the invention, a thicker the frustule, or a layer of a frustules is, longer pores are provided within the frustules. The longer the pores are, the better the uptake of e.g. light are. The thick frustules of the benthic pennate diatoms make them promising for solar cell applications.

According to at least one example embodiment of the invention the, pores of the different layers of the frustules forms a funnel-like structure which allows for an efficient uptake of light and enhances the intensity of the light. It shall be understood that this funnel-like structure may be one of the structures that is kept by keeping the calcination temperature below 450° C.

According to at least one example embodiment of the invention the frustules extracted from benthic pennate diatoms uptakes light which is reflected in to the pores of the frustules extracted from benthic pennate diatoms. In other words, the frustules may be used for uptake of light which has previously been reflected by themselves.

According to at least one example embodiment of the invention the frustules of the benthic pennate diatoms is thicker than the frustules of pelagic pennate diatoms. This means that the uptake of light may be larger if it is done by frustules of benthic pennate diatoms than by frustules from suspension living diatoms. In addition, the frustules of benthic pennate diatoms are thicker than the frustules of the centric diatom.

According to at least one example embodiment of the invention the frustules extracted from benthic pennate diatoms are provided as a layer on top of a solar panel. The solar cell can be chosen from a list comprising but not limit to: silicon solar cells, dye-sensitized solar cells, thin film solar cell, polymer based solar cells. According to at least one example embodiment of the invention the frustules extracted from benthic pennate diatoms may be provided inside of the solar cell, in the active layer.

According to at least one example embodiment of the invention, the frustules is provided as a layer on top of said solar cell or said solar panel, such that incident light passes through said layer of frustules before reaching said solar cell and/or solar panel and/or that the incident light is guided by said layer of frustules towards said solar cell and/or solar panel.

According to at least one example embodiment of the invention, the solar cell and/or solar panel is a silicon based solar cell and/or solar panel. It shall be understood that a silicon based solar cell is a solar cell where the active layer comprises silicon, i.e. the silicon is the light absorbing material. Likewise, a silicon based solar panel is a solar panel where the active layer comprises silicon. In other words, the method comprises the step of depositing said frustules on top of a silicon based solar cell and/or solar panel.

In other words, the method comprises the step of depositing the frustules extracted from benthic pennate diatoms on top of a silicon based solar cell, wherein said frustules are deposited such that the incident light passes through said layer of frustules before reaching an active layer of said solar cell and/or said solar panel.

According to at least one example embodiment the silicon based solar cell and/or solar panel comprises crystalline silicon, e.g. monocrystalline silicon or polycrystalline silicon.

According to at least one example embodiment of the invention, the solar cell may be a single junction solar cell or a multi-junction solar cell.

According to at least one example embodiment of the invention, the frustules is provided as a monolayer or as several layer on top of the solar cell or the solar panel.

According to at least one example embodiment of the invention, the monolayer partially or fully covers the surface.

According to at least one example embodiment of the invention, the frustules extracted from benthic pennate diatoms covers no more than 20%, or no more than 15%, or no more than 10% of the surface of said silicon based solar cell or solar panel. Alternatively, or additionally, the frustules cover at least 2%, or at least 3%, or at least 5% of the surface of said silicon based solar cell or solar panel. For example, the frustules may cover 2-20%, or 3-10%, of the surface of the solar cell or solar panel.

According to an alternative embodiment, the frustules may cover up to 100% of the surface of said silicon based solar cell or solar panel, e.g. they may cover at least 50%, or at least 60%, or at least 70%, or at least 80%, or at least 90% of the surface of the silicon based solar cell. For example, the frustules may be provided with printing techniques, e.g. inkjet printing, 3D printing and/or bioprinting which may provide the frustules in a manner that they do not cover each other even at higher surface coverage.

According to at least one example embodiment of the invention the funnel-like structure of the pores of the frustules effectively capture light and guides it towards the surface of the solar cell or solar panel and thereby increases the efficiency of the solar cell or solar panel.

According to at least one example embodiment of the invention, said frustules are mixed with a second material. The second material may for example be titanium dioxide.

According to at least one example embodiment of the invention, the solar cell or solar panel is a dye sensitized solar cell or solar panel.

According to at least one example embodiment of the invention the frustules is provided as a part of an active layer, e.g. as mixed with e.g. titaniumdioxide, of said dye sensitized solar cell or solar panel.

According to at least one example embodiment of the invention the layer provided on top of a solar cell works as an anti-reflection layer and hence, more light can be converted to electricity by the solar cell as compared with a solar cell without a layer of benthic pennate diatoms.

According to at least one example embodiment of the invention the frustules extracted from benthic pennate diatoms are provided in the active layer of the solar cell. The active layer may be the light-absorbing layer of the solar cell. The active layer can for example comprise semi-conducting polymer, semi-conducting small molecules and/or dye molecules.

According to at least one example embodiment of the invention the frustules extracted from benthic pennate diatoms uptake mechanical waves which are sound waves and the absorption of sound waves are used for sound insulation.

According to at least one example embodiment of the invention the frustules extracted from benthic pennate diatoms can be used for sound insulation in for example buildings, e.g. in the walls, ceilings or floors.

According to at least one example embodiment of the invention the frustules extracted from benthic pennate diatom uptake a chemical substance and wherein said absorption of chemical substances can be used in biosensors.

According to at least one example embodiment of the invention the chemical substances can for example be water and/or proteins.

According to at least one example embodiment of the invention an absorbed chemical substance is released in a controlled manner by said frustules extracted from benthic pennate diatoms.

According to at least one example embodiment of the invention the controlled released means that the chemical substance, e.g. water and/or proteins, which has been taken up by the benthic pennate diatoms, is released.

According to at least one example embodiment of the invention the frustules extracted from benthic pennate diatoms are used for heat insulation.

According to at least one example embodiment of the invention the frustules extracted from benthic pennate diatoms are provided as an aerogel. The aerogel forms a porous layer of the benthic pennate diatoms. This layer does not conduct heat due to the air within the layer and therefore this layer can be used as heat insulation. According to at least one example embodiment of the invention the insulation formed by the aerogel is thinner than other heat insulations layer normally is.

According to at least one example embodiment of the invention the frustules extracted from benthic pennate diatoms are provided as a dry powder wherein said dry powder are mixed with a second material forming a composite material.

According to at least one example embodiment of the invention the composite material is used for light weight products. Light weight products may be achieved due to high strength-to-weight ratio.

According to a second aspect of the invention use of frustules extracted from benthic pennate diatoms in a solar cell and/or solar panel are provided.

Effects and features of this second aspect of the present invention are largely analogous to those described above in connection with the first aspect of the inventive concept. Embodiments mentioned in relation to the first aspect of the present invention are largely compatible with the second aspect of the invention.

According to at least one example embodiment of the invention, said frustules may be extracted from benthic pennate diatoms according to the method as described in accordance with the first aspect of the invention, wherein said benthic pennate diatoms are cultured according to the method as described above.

According to at least one example embodiment of the invention, said solar cell and/or solar panel is a silicon based solar cell and/or solar panel.

According to at least one example embodiment of the invention, the frustules is provided as a layer on top of said solar cell and/or said solar panel, such that incident light passes through said layer of frustules before reaching said solar cell and solar panel.

According to at least one example embodiment of the invention, the solar cell or solar panel is a dye sensitized solar cell or solar panel.

According to at least one example embodiment of the invention, the frustules is mixed with titanium dioxide and is provided as a part of an active layer of said dye sensitized solar cell or solar panel.

According to an alternative aspect of the invention frustules extracted from benthic pennate diatoms are provided. The benthic pennate diatoms have been cultured through an industrial biofilm process in which said benthic pennate diatoms are grown on a surface in a water compartment and wherein said benthic pennate diatoms are harvested from said surface Effects and features of this alternative aspect of the present invention are largely analogous to those described above in connection with the first and the second aspects of the inventive concept. Embodiments mentioned in relation to the first and the second aspect of the present invention are largely compatible with this alternative aspect of the invention.

According to at least one example embodiment the frustules extracted from benthic pennate diatoms is used in various applications.

According to at least one example embodiment of the invention, the frustules extracted from benthic pennate diatoms are provided in a liquid medium and/or as a dry product.

According to at least one example embodiment of the invention, the frustules extracted from benthic pennate diatoms provided in a liquid medium is deposited on a surface using a coating method.

According to at least one example embodiment of the invention, the frustules extracted from benthic pennate diatoms are used for absorbing energy, chemical substances and/or mechanical waves.

According to at least one example embodiment of the invention, the frustules extracted from benthic pennate diatoms absorbs energy which corresponds to wavelengths within the infrared range, within the visible range and/or within the ultraviolet range, and wherein said energy absorption is used for enhancing the efficiency in solar cells.

According to at least one example embodiment of the invention, the frustules extracted from benthic pennate diatoms absorbs mechanical waves which are sound waves and the absorption of sound waves are used for sound insulation.

According to at least one example embodiment of the invention, the frustules extracted from benthic pennate diatom absorbs a chemical substance and wherein said absorption of chemical substances can be used in biosensors.

According to at least one example embodiment of the invention, an absorbed chemical substance is released in a controlled manner by said frustules extracted from benthic pennate diatoms.

According to at least one example embodiment of the invention, the frustules extracted from benthic pennate diatoms are used for heat insulation.

According to at least one example embodiment of the invention, the frustules extracted from benthic pennate diatoms are provided as a dry powder and wherein said dry powder are mixed with a second material forming a composite material. Generally, all terms used in the claims are to be interpreted according to their ordinary meaning in the technical field, unless explicitly defined otherwise herein. All references to "a/an/the element, device, component, means, step, etc." are to be interpreted openly as referring to at least one instance of said element, device, component, means, step, etc., unless explicitly stated otherwise.

BRIEF DESCRIPTION OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein.

DETAILED DESCRIPTION OF THE DRAWINGS

In the present detailed description, embodiments of frustules extracted from benthic pennate diatoms and use of the same are discussed. It should be noted that this by no means limits the scope of the invention, which is also applicable in other circumstances for instance with other types or variants of frustules extracted from benthic pennate diatoms than the embodiments shown in the appended drawings. Further, that specific components are mentioned in connection to an embodiment of the invention does not mean that those components cannot be used to an advantage together with other embodiments of the invention.

The frustules extracted from benthic pennate diatoms according to the invention can advantageously be used for in several applications. The industrial biofilm process provides a controlled way to grow and harvest the desired species of benthic pennate diatom, from which the frustules are being extracted.

Figure 1A:
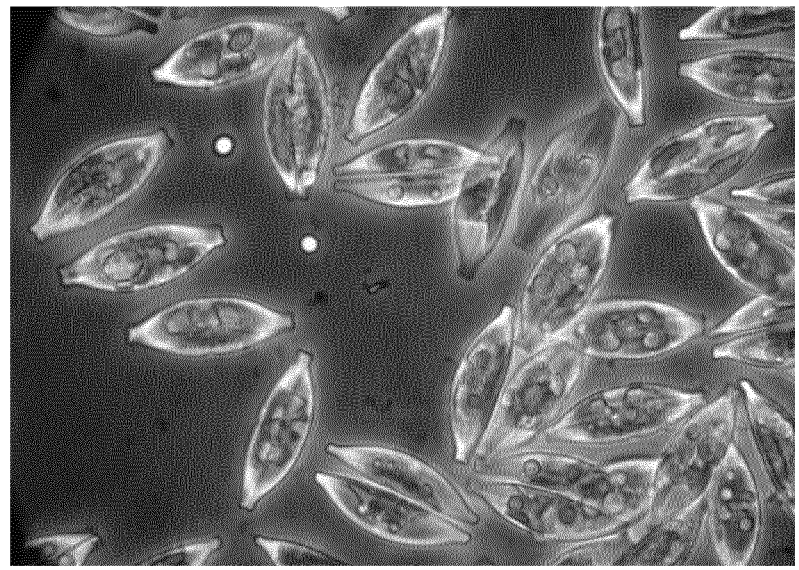
FIG. 1a is a micrograph of benthic pennate diatoms in accordance with at least one embodiment of the invention.

FIG. 1a shows benthic pennate diatoms which have been cultured through an industrial biofilm process. The benthic pennate diatoms are grown on a surface in a water compartment and the benthic pennate diatoms are harvested from said surface. The said benthic pennate diatoms are provided in a liquid medium and/or as a dry product.

Figure 1B:
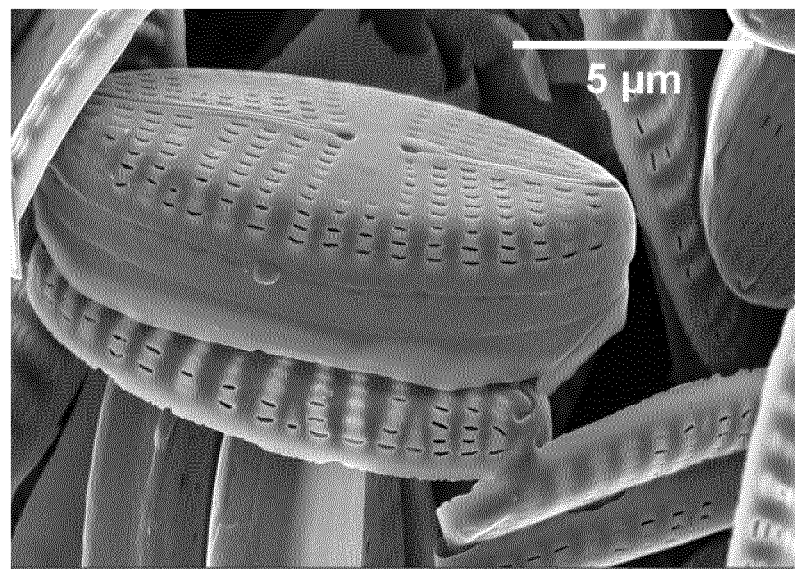
FIG. 1b is a SEM image of frustules extracted from benthic pennate diatoms in accordance with at least one embodiment of the invention.

FIG. 1b shows frustules extracted from said benthic pennate diatoms.

According to at least one example embodiment of the invention the frustules extracted from benthic pennate diatoms are used for uptake of energy, chemical substances and/or mechanical waves.

Figure 2:
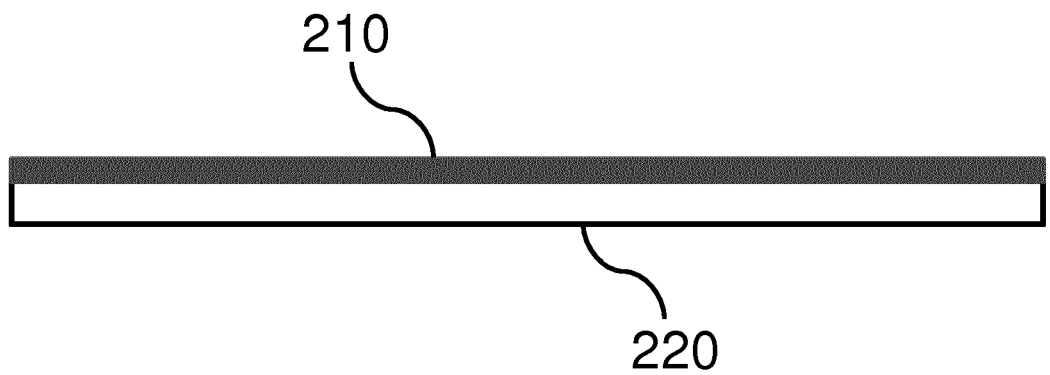
FIG. 2 shows a cross-sectional view of a surface coated with frustules extracted from benthic pennate diatoms according to at least one embodiment of the invention.

FIG. 2 shows a cross-sectional view of frustules extracted from benthic pennate diatoms 210 provided in a liquid medium and deposited on a surface 220 by the use a coating method.

According to at least one example embodiment of the invention the frustules extracted from benthic pennate diatoms 210 provided in a liquid medium. The frustules extracted from benthic pennate diatoms are being deposited on a surface 220 with a coating method which is chosen from a list comprising but not limited to: doctor blading, spin-coating, roller coating, screen printing, spray coating and dip coating According to at least one example embodiment of the invention such frustules extracted from benthic pennate diatoms 210 being deposited on a surface 220 may be used for uptake of energy which corresponds to wavelengths within the infrared range, within the visible range and/or within the ultraviolet range. This may for example be used for enhancing the efficiency in solar cells.

According to at least one example embodiment of the invention such frustules extracted from benthic pennate diatoms 210 being deposited on a surface 220 are used for absorption of mechanical waves are sound waves and the absorption of sound waves is used for sound insulation.

According to at least one example embodiment of the invention such frustules extracted from benthic pennate diatoms 210 is used for uptake of a chemical substance 220 and wherein said absorption of chemical substances can be used in biosensors.

According to at least one example embodiment of the invention the uptaken chemical is released in a controlled manner by said frustules extracted from benthic pennate diatoms.

According to at least one example embodiment of the invention such frustules extracted from benthic pennate diatoms 210 being deposited on a surface 220 are used for heat insulation.

Figure 3:
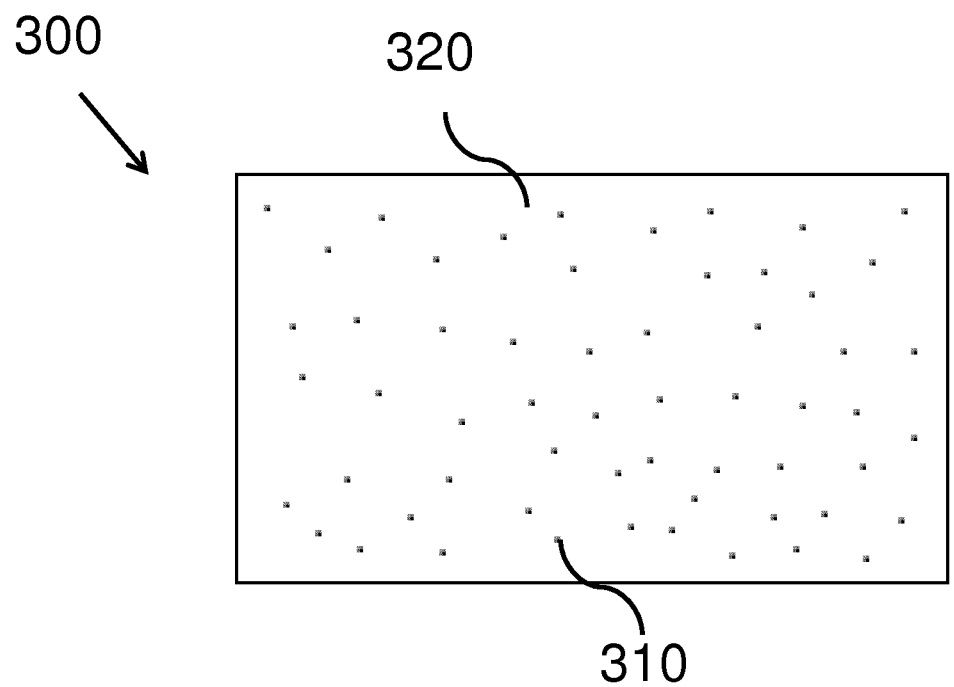
FIG. 3 shows a cross-sectional view of a composite containing frustules extracted from benthic pennate diatoms in accordance with at least one embodiment of the invention.

FIG. 3 shows a composite material 300 where the frustules extracted from benthic pennate diatoms 310 provided as a dry powder has been mixed with a second material forming a composite material 320.

The skilled person realizes that a number of modifications of the embodiments described herein are possible without departing from the scope of the invention, which is defined in the appended claims.

Figure 4:
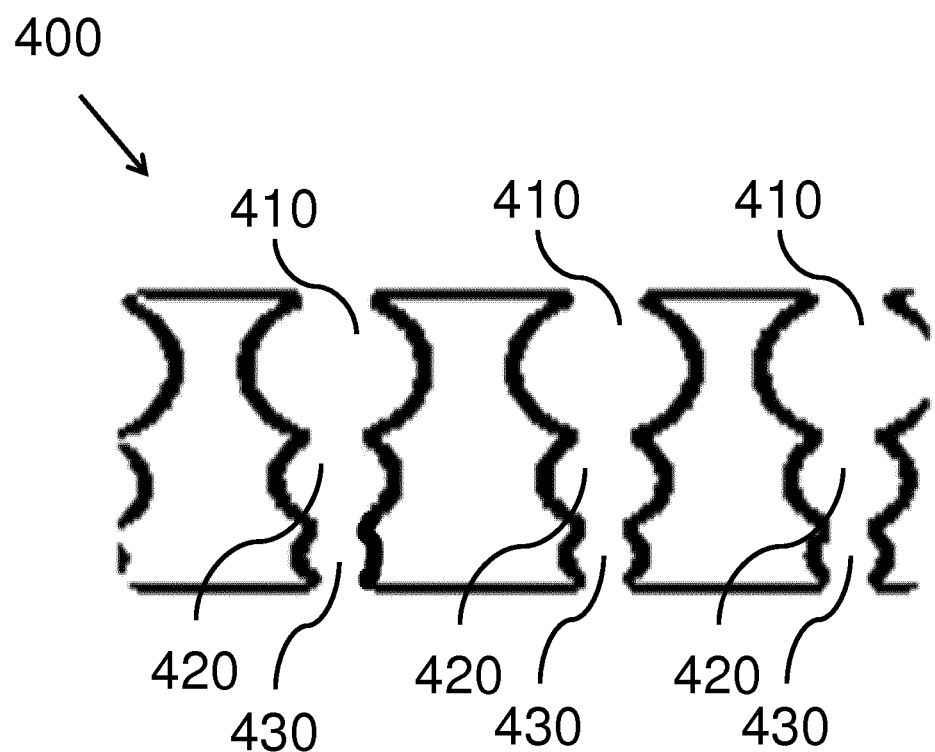
FIG. 4 shows a schematic and cross-sectional view of a frustule extracted from a benthic pennate diatom in accordance with at least one example embodiment of the invention.

FIG. 4 shows a cross-sectional view of a frustule extracted from a benthic pennate diatom 400. The frustule comprises several layers, which in FIG. 4 is three. The different layers comprises pores 410, 420, 430 of different sizes. Here, the lowest layer comprises the smaller pores 430, whereas the top layer comprises the largest pores 410. The middle layer comprises pores 420 of a size which is between the pores 410, 430 of the lowest and the top layer. The pores 410, 420, 430 forms a funnel-like structure which may be used for uptake energy (e.g. light), mechanical waves and/or chemicals. The thickness of the frustule 400, or of the different layers defines the sizes of the pores.

Example 1 Solar Cell Application

Method:
  TEC15 glass was used for all working electrodes. All electrodes were screen printed and sintered under identical conditions and settings.
  A ratio of 1:50 (frustules:titanium dioxide) was used in all the mixed cells boths those containing frustules from benthic pennate diatoms and those containing frustules from fossil diatoms.
  D35 were used as dye and standard iodide electrolyte containing ionic liquid where used as electrolyte for all cells (MPN as solvent).

The incident photon-to-current efficiency (IPCE) measurements were conducted between 350-800 nm, and three cells were measured for each series.

Results:

According to the incident photon-to-current efficiency (IPCE) measurements the dye sensitized solar cells with frustules extracted from benthic pennate diatoms mixed with titanium dioxide perform better than a reference dye sensitized solar cell with only titanium dioxide. Solar cells with frustules from fossil diatoms mixed with titanium dioxide perform similar to the reference dye sensitized solar cell.

On average, relative to the reference dye sensitized solar cell, the solar cells with frustules extracted from benthic pennate diatoms perform approximately 60% better and the solar cells with frustules from fossil diatoms perform 9% better than the reference dye sensitized solar cell.

Example 2 Solar Cell Application

Method

Commercial solar cells (BP Solar 0.446W Polycrystalline Photovoltaic Solar Panel) were used for all tests. The solar cell performances were measured 'as received' as references. In order to achieve a stable and monolayer coating, the cell surfaces were plasma cleaned (oxygen plasma) and treated with an amino-silane monolayer via vapour phase deposition ((3-Aminopropyl)triethoxysilane, APTES) at 70 ☐ C. All deposition tests on solar panels were performed with the same batch of NSFD powder (Batch 3C). NSFD dispersion of 0.2 wt. % was prepared by weighing 0.06 g of the calcined powder and dispersing it in 30 mL of 1 wt. % solution of TritonX100 in milliQ water. This was placed under magnetic stirring overnight. Thereafter, the dispersion was centrifuged at 2.5 krpm; (1467 g) for 2 minutes and the supernatant was replaced with fresh milliQ water. This process was repeated and the final milliQ dispersion was labelled Disp. A. An aliquot of Disp. A was diluted to 0.01 wt. % (Disp. B). Another dispersion of the NSFD powder was prepared in ethanol with a concentration of 0.1 wt. % (Disp. C). The solar cell surfaces were coated by a adding 5 mL of the dispersions to cover the entire surface and allowed to settle for 2 hours. Thereafter the dispersions were drained out and the surfaces were rinsed with the solvent. The solar cells were dried in at 50° C. Any residual patches of dry powder were removed with a jet of compressed N2 flow. This resulted in a monolayer of the dispersion, with a particle density depending on the dispersion used for coating. As a control sample, a solar cell was plasma cleaned, treated with APTES monolayer and then pure solvent was used instead of the NSFD dispersion, followed by oven drying. From image analysis of the microscopy images of Cell 4, Cell 6 and Cell 8, we found that the disperse coating had a coverage of 7.8%, the intermediate coating had a coverage of 31.1%, and dense coating had a coverage of 79.4%.

Summary

In summary, I-V data of cell coated with the least disperse coating showed an improvement in output power of 3.7% after coating, when compared to the output power before coating, when measured under the same input optical power. The NSFD particles covered about 7.8% of the surface area. Denser coatings showed negligible improvement in output power (0.3% for intermediate and −0.7% for dense) when comparing the before and after coating performances. Since the input power, which is the lamp irradiance, was adjusted to be equal, this difference in output power corresponds to difference in performance efficiency of the cells.

The invention claimed is:

1. A method for obtaining frustules from benthic pennate diatoms comprising the steps of:
   culturing benthic pennate diatoms in an biofilm process, wherein in said biofilm process said benthic pennate diatoms are growing on at least one surface in a water-comprising compartment and wherein said benthic pennate diatoms form a biofilm on said at least one surface;
   harvesting said benthic pennate diatoms from said at least one surface, said benthic pennate diatoms being in an exponential growth phase;
   extracting frustules from the harvested benthic pennate diatoms by separating said frustules from organic biomass comprised in said benthic pennate diatoms.

2. The method according to claim 1, wherein said water-comprising compartment is a pool.

3. The method according to claim 1, wherein said water-comprising compartment comprises at least one of:
   a nutritious water with a concentration of from 0.01 to 500 $g/m^3$ nitrogen and/or from 0.01 to 100 $g/m^3$ phosphorous; and
   a silicon compound added to the water in said water-comprising compartment such that the concentration of silicon in the water in said water-comprising compartment is in the range of 0.01-100 $g/m^3$.

4. The method according to claim 3, wherein said culturing is performed in waste water.

5. The method according to claim 4, wherein the water is received from a fish farm, the food or biomass industry and/or household waste water.

6. The method according to claim 2, wherein the water comprising compartment is a shallow pool comprising water at a depth of no more than 0.5 m.

7. The method according to claim 1, wherein several water comprising compartments are arranged stacked on top of each other.

8. The method according to claim 1, wherein the at least one surface is a horizontal surface.

9. The method of claim 3, wherein the silicon compound is $Na_2SiO_3.5H_2O$ or $Na_2SiO_3.9H_2O$.

* * * * *